United States Patent [19]
Buysch et al.

[11] Patent Number: 5,185,467
[45] Date of Patent: Feb. 9, 1993

[54] PROCESS FOR THE PREPARATION OF 2,2-BIS-(AMINOPHENYL)-PROPANE

[75] Inventors: Hans-Josef Buysch, Krefeld; Dieter Arlt, Cologne, both of Fed. Rep. of Germany

[73] Assignee: Bayer Aktiengesellschaft, Leverkusen, Fed. Rep. of Germany

[21] Appl. No.: 772,815

[22] Filed: Oct. 8, 1991

[30] Foreign Application Priority Data

Oct. 18, 1990 [DE] Fed. Rep. of Germany ....... 4033099

[51] Int. Cl.$^5$ ............................................ C07C 209/36
[52] U.S. Cl. ..................................................... 564/330
[58] Field of Search ........................................ 564/330

[56] References Cited
U.S. PATENT DOCUMENTS 5,037,994  8/1991  Mossman et al. .................... 564/419

OTHER PUBLICATIONS

Journal of the American Chemical Society, Bd. 32, Mar. 1930, pp. 1122–1127.
Kervennal et al, Chemical Abstracts, vol. 102 (1985) 79426z.
Kervennal et al, Chemical Abstracts, vol. 104 (1986) 34839m.

Primary Examiner—Richard L. Raymond
Attorney, Agent, or Firm—Sprung Horn Kramer & Woods

[57] ABSTRACT

2,2-Bis-(aminophenyl)-propane having a content of the 4,4'-isomers of at least 70% can be prepared by nitrating 2,2-diphenyl-propane to give 2,2-bis-(nitrophenyl)-propane and reducing the latter in a subsequent step to give 2,2-bis-(aminophenyl)-propane.

8 Claims, No Drawings

PROCESS FOR THE PREPARATION OF 2,2-BIS-(AMINOPHENYL)-PROPANE

The present invention relates to a process for the preparation of 2,2-bis-(aminophenyl)-propane having a content of the 4,4,-isomer of at least 70% by nitration of 2,2-diphenyl-propane and subsequent reduction.

2,2-Bis-(4-aminophenyl)-propane is an interesting starting material for the preparation of polymers, such as fibres (Makromol. Chem. 32, (1959), 1-12), epoxy resins (U.S. Pat. No. 2,989,498; CS 177,664, cited by C.A. 92 (1980), 59 771e), polyamidoimides (JP 73/11,826, cited by C.A. 80 (1974) 84 401u), or of anticorrosive agents (Vopr. Khim. Khim. Tekhnol. 67 (1982), 65-68, cited by C.A. 100 (1984), 37 873w).

Suitable syntheses for diaminodiphenylpropane have therefore been sought. The best-known synthesis hitherto appears to be the condensation of aniline with acetone. Thus, according to U.S. Pat. No. 3,670,024, diaminodiphenylpropane is obtained by condensation of aniline hydrochloride with acetone. Although the yield can be up to 73% of the theoretical yield, the process has the disadvantage that large amounts of sodium chloride are produced as a by-product.

It has now been found that very high yields of 2,2-bis-(aminophenyl)-propane are obtained when 2,2-diphenylpropane is nitrated to give 2,2-bis-(nitrophenyl)-propane and in a second step the latter is reduced to 2,2-bis-(aminophenyl)-propane. The 2,2-bis-(4-amino-phenyl)-propane particularly desired can be obtained here in yields of up to over 80%, but of at least 70% of the theoretical yield. This is to a large extent surprising, since the nitration and reduction of analogous diphenylalkanes essentially gives other yields and isomer distributions. Thus, 32–55% (according to exemplary embodiment 48%) of the 4,4'-dinitrodiphenylmethane is obtained by nitration of diphenylmethane according to a particularly optimised process (EP 125,169), a whole series of isomers nitrated in the 2,2'- and 3,3'-position additionally being formed. Diphenylethane likewise yields mixtures of the various isomers and only 33 to 55% of the 4,4'-isomer (J. Am. Chem. Soc. 52 (1930) 1122; EP 149,388) during the nitration.

The invention relates to a process for the preparation of 2,2-bis-(aminophenyl)-propane having a content of the 4,4'-isomer of at least 70%, which is characterised in that 2,2-diphenylpropane is nitrated to give 2,2-bis-(nitrophenyl)-propane and the latter is reduced in a subsequent step to 2,2-bis-(aminophenyl)-propane.

The starting material for the process according to the invention is 2,2-diphenylpropane. This compound is accessible in various ways. Good yields are obtained, for example, by reaction of α-chloro-isopropylbenzene with benzene in the presence of Lewis acids, in particular in the presence of aluminium chloride.

Owing to the good accessibility of the starting material diphenylpropane and the good yield of diaminodiphenyl-propane, the process according to the invention is superior to those hitherto.

Suitable nitrating agents are, for example, concentrated and highly concentrated nitric acids having a content of 50–100% $HNO_3$, for example the aqueous $HNO_3$ boiling as an azeotrope and mixtures of nitric acids with sulphuric acids, it being possible for the sulphuric acids to contain either up to 20% by weight of water or up to 20% by weight of $SO_3$, or mixtures of sulphuric acid and nitrates of the alkali metals or alkaline earth metals, such as sodium nitrate, potassium nitrate or calcium nitrate. Preferentially, $HNO_3/H_2SO_4$ mixtures of the various concentrations (so-called nitrating acid) are employed. In such nitric acids, the $HNO_3$ can contain up to 60% by weight of water and the $H_2SO_4$ can have the above-mentioned composition.

Diphenylpropane can be employed for nitration either with or without solvent. Preferentially, it is employed with a solvent. Solvents suitable for this purpose must be inert under the reaction conditions and easy to separate by distillation. Solvents which may be mentioned are those from the group comprising the aliphatic hydrocarbons, the aliphatic halogenohydrocarbons and the nitroaromatics. Individual representatives are, for example, cyclohexane, heptane, isooctane, isononane, isododecane, dichloromethane, trichloromethane, tetrachloromethane, dichloropropane, chlorobutane, dichlorobutane, chlorocyclohexane, nitrobenzene and nitrotoluenes. Preferentially, aliphatic hydrocarbons and aliphatic chlorohydrocarbons are employed.

The molar ratio of 2,2-diphenylpropane to the nitrating reagent containing the nitro group is 1:2–15, preferably 1:2–5. Using such a molar ratio, the two necessary nitro groups can be introduced into the 2,2-diphenylpropane and a complete conversion of the starting material thus achieved. However, it is basically possible also to employ sub-stoichiometric amounts of nitrating reagent if complete conversion of the starting material is not desired.

The temperature for the nitration can vary within wide limits, for example from 0° to 150° C. Within this temperature range, with highly concentrated nitrating reagent the lower range will be selected and conversely. Thus, when using concentrated acids the reaction will be carried out at 0° to 80° C., preferably even at 0 to 60° C. Conversely, when using less highly concentrated acids, for example those under 80% by weight (the remainder up to 100% is water) the reaction can be carried out in a high temperature range; thus, for example, it is possible in such a case to work under adiabatic conditions up to temperatures of 120° to 150° C., preferably 120° to 140° C., in order to utilize the heat of nitration (cf. Houben-Weyl, 4th edition, volume 10/1, (1971), pp. 479–488).

The yield of dinitro compound is virtually quantitative if the supply of nitrating reagent is adequate. The reaction product is as a rule isolated by separating off and evaporating the organic phase. However, the reaction can also be carried out in solvents in which the dinitro compound, in particular the 4,4'-isomer, is poorly soluble, precipitates on cooling and can easily be separated by filtration. The aliphatic hydrocarbons and the aliphatic halogenohydrocarbons already mentioned above are in particular suitable for this purpose.

The crude nitration product can be employed immediately for the subsequent reduction. However, a separation of the isomers in the manner mentioned can also be carried out before the reduction and the isomers reduced separately.

The reduction of the dinitro-diphenylpropanes is carried out by methods known per se. Mixtures of base metals and acids, mixtures of hydrazine and hydrogenation catalysts, mixtures of sulphides or $H_2S$ and dithionites or catalytically activated hydrogen can be employed for this purpose. Preferentially, hydrazine or catalytically activated hydrogen is employed. Hydrogenation catalysts are, for example, palladium or platinum or their oxides or other noble metals on supports, such as carbon or γ-alumina, or Raney metals, such as Raney nickel. Such hydrogenation catalysts are known to the person skilled in the art, for example, from Houben-Weyl, 4th edition, volume 11/1 (1957), pp. 363-382, 394-406, 409-442, 454-457 and 462-472.

In the case of hydrogenation with catalytically activated hydrogen, the reaction can be carried out batchwise or continuously, for example in a batch process or in the liquid phase. The temperatures are in this case 0° to 200° C., preferably 20° to 150° C. The hydrogen pressures are 1 to 100 bar, preferably 2 to 50 bar. The reaction is carried out with an excess of hydrogen. The excess is in this case 0.2 to 20 mol of $H_2$, preferably 1 to 10 mol of $H_2$, per mole of dinitro-diphenylpropane over the amount of $H_2$ necessary for complete hydrogenation of the nitro groups.

The reduction product obtained is separated off from the reducing agent, catalysts and the other reaction products by filtering or washing out and can be used directly for some purposes, for example for phosgenation to the diisocyanate or for epoxy resin curing. In the case of particular demands on the purity, it can be purified in a customary manner by distillation or recrystallisation (cf. U.S. Pat. No. 3,670,094).

EXAMPLE 1

541 g of 2-chloro-2-phenylpropane (3.5 mol) were added dropwise at 5° C. with stirring to a suspension of 35 g of clean pulverised aluminium chloride in 3.5 l of dry benzene in the course of 5 h, and the mixture was kept at 5° C. for a further 15 min. and then poured onto ice. The benzene phase was neutralised with potassium carbonate after separating off the aqueous phase, dried and freed from excess benzene. 650 g of crude product were obtained, which was fractionally distilled through a column about 100 cm long. 527 g (78% of the theoretical yield) of 2,2-diphenylpropane passed over at 152°-160° C. and 20 mbar.

EXAMPLE 2

135 g of water were added to a solution of 490 g (2.5 mol) of 2,2-diphenylpropane in 500 ml of chloroform and a mixture of 935 g (6.75 mol) of commercial nitric acid boiling as an azeotrope and 2,000 g of concentrated sulphuric acid were added dropwise at 0° to 10° C. with stirring in the course of 1-2 h, the mixture was allowed to subsequently react for 30 min. and was poured onto 3 kg of ice, the chloroform phase was separated and the aqueous phase was extracted twice more with chloroform. The combined chloroform phases were washed with water, dried with sodium sulphate and evaporated: 688 g of crude product (99% of the theoretical yield) having an N content of 9.73 to 9.80 (calculated for dinitro compound: 9.78%) and a content of 2,2-bis-(4-(nitrophenyl)-propane of 80%. The 4,4'-isomer could be obtained pure (m.p. 135°-6° C.) by recrystallising from toluene, xylene or cyclohexane/toluene.

EXAMPLE 3

10 g of Raney nickel were added to 94 g (0.329 mol) of 2,2-bis-(4-nitrophenyl)-propane in 250 ml of dioxane, the mixture was warmed to 50° C. and 84 g (1.3 mol) of 50% strength hydrazine were added dropwise in the course of 1-2 h. After the completion of the exothermic reaction, the mixture was heated at 60° C. until the evolution of gas ceased. The mixture was filtered off from the Raney nickel and evaporated. The residue of 74 g (100% of the theoretical yield) of brown crystalline product was purified by distillation. At 172°-188° C./0.5 mbar, 72 g (97% of the theoretical amount) of a distillate which solidified to give colourless crystals (m.p. 129°-131° C.) passed over.

We claim:

1. Process for the preparation of 2,2-bis-(aminophenyl)-propane having a content of the 4,4'-isomer of at least 70%, wherein 2,2- diphenyl-propane is nitrated in a solvent selected from the group consisting of aliphatic hydrocarbons and aliphatic halogeno-hydrocarbons to give 2,2-bis-(nitrophenyl)-propane and the latter is reduced in a subsequent step to 2,2-bis-(aminophenyl) -propane.

2. Process according to claim 1 wherein the nitrating agent used is 50-100% strength $HNO_3$, $HNO_3/H_2SO_4$ mixtures or mixtures of $H_2SO_4$ and nitrates of the alkali metals or alkaline earth metals.

3. Process according to claim 2, wherein the $HNO_3$ in the $HNO_3/H_2SO_4$ mixture can contain up to 60% by weight of $H_2O$ and the $H_2SO_4$ can contain up to 20% by weight of $H_2O$ or up to 20% by weight of $SO_3$.

4. Process according to claim 1 wherein the molar ratio of 2,2-diphenylpropane to the nitrating reagent containing the nitro group is 5. Process according to claim 1, wherein the nitration is carried out at a temperature of 0° to 150° C.

6. Process according to claim 1, wherein mixtures of base metals and acids, mixtures of hydrazine and hydrogenation catalysts, mixtures of sulphides or hydrogen sulphide and dithionites or catalytically activated hydrogen, are employed for the hydrogenation.

7. Process according to claim 6 wherein hydrogenation is carried out using catalytically activated hydrogen at 0° to 200° C., and at an $H_2$ pressure of 1 to 100 bar 8. Process according to claim 7 an Hhd 2 excess of 0.2 to 20 mol of $H_2$, per mole of dinitro-diphenylpropane over the amount of $H_2$ necessary for the complete hydrogenation of the nitro groups is employed.

* * * * *

UNITED STATES PATENT AND TRADEMARK OFFICE
CERTIFICATE OF CORRECTION

PATENT NO. : 5,185,467
DATED : February 9, 1993
INVENTOR(S) : Buysch et al.

It is certified that error appears in the above-identified patent and that said Letters Patent is hereby corrected as shown below:

Col. 4, line 39   After " group is " insert -- 1:2-15 . --

Col. 4, line 47   After "wherein " insert -- the --

Col 4, line 50    Delete " an Hhd 2 " and substitute -- wherein -- an $H_2$ --

Signed and Sealed this

Nineteenth Day of July, 1994

*Attest:*

BRUCE LEHMAN

*Attesting Officer*  *Commissioner of Patents and Trademarks*